United States Patent
Danley

(10) Patent No.: US 9,857,241 B2
(45) Date of Patent: Jan. 2, 2018

(54) QUASIADIABETIC DIFFERENTIAL SCANNING CALORIMETER

(71) Applicant: Waters Technologies Corporation, Milford, MA (US)

(72) Inventor: Robert L. Danley, Collingswood, NJ (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 330 days.

(21) Appl. No.: 14/425,473

(22) PCT Filed: Aug. 30, 2013

(86) PCT No.: PCT/US2013/057438
§ 371 (c)(1),
(2) Date: Mar. 3, 2015

(87) PCT Pub. No.: WO2014/039376
PCT Pub. Date: Mar. 13, 2014

(65) Prior Publication Data
US 2015/0253206 A1 Sep. 10, 2015

Related U.S. Application Data

(60) Provisional application No. 61/696,488, filed on Sep. 4, 2012.

(51) Int. Cl.
*G01K 17/00* (2006.01)
*G01N 25/00* (2006.01)
(Continued)

(52) U.S. Cl.
CPC .............. *G01K 17/08* (2013.01); *G01N 25/20* (2013.01); *G01N 25/4833* (2013.01)

(58) Field of Classification Search
CPC ........... G01N 25/4866; G01N 25/4833; G01N 25/20; G01K 17/08
(Continued)

(56) References Cited

U.S. PATENT DOCUMENTS 5,672,289 A   9/1997  O'Neill
6,390,669 B1  5/2002  Nakamura et al.
(Continued)

FOREIGN PATENT DOCUMENTS

EP   1 139 083 A1   10/2001
WO   2012/103601 A1  8/2012

OTHER PUBLICATIONS

Extended European Search Report for Application No. 13835434.5, dated Jun. 7, 2016 (7 pages).
(Continued)

*Primary Examiner* — An Do
(74) *Attorney, Agent, or Firm* — Schmeiser, Olsen & Watts LLP

(57) ABSTRACT

A method of operating a differential scanning calorimeter wherein errors in the heat flow rate measurement are reduced by operating the calorimeter in a quasiadiabatic mode and by employing a heat flow rate measurement algorithm that includes the leakage heat flow rate. The temperature of the DSC enclosure is controlled independently of the temperature of the measuring system, which allows the temperature difference between the sample and reference containers and the enclosure to be minimized, thus minimizing leakage heat flow.

17 Claims, 5 Drawing Sheets

(51) Int. Cl.
*G01K 17/08* (2006.01)
*G01N 25/48* (2006.01)
*G01N 25/20* (2006.01)

(58) Field of Classification Search
USPC ............... 702/127, 130, 136; 374/10, 11, 14
See application file for complete search history.

(56) References Cited

U.S. PATENT DOCUMENTS

| | | | |
|---|---|---|---|
| 6,431,747 B1 | 8/2002 | Danley | |
| 6,488,406 B2 | 12/2002 | Danley | |
| 6,578,367 B1 | 6/2003 | Schaefer et al. | |
| 6,843,595 B2 | 1/2005 | Danley | |
| 7,025,497 B2 | 4/2006 | Danley | |
| 7,306,365 B2 | 12/2007 | Danley | |
| 7,470,057 B2 | 12/2008 | Danley | |
| 7,802,916 B2 * | 9/2010 | Teramoto | G01N 25/20 374/1 |
| 8,496,374 B2 * | 7/2013 | Nishimura | G01N 25/4866 374/10 |
| 2003/0072348 A1 * | 4/2003 | Danley | G01K 17/00 374/31 |
| 2006/0187998 A1 | 8/2006 | Danley | |
| 2008/0052032 A1 | 2/2008 | Danley | |
| 2009/0034579 A1 * | 2/2009 | Schick | G01N 25/4866 374/10 |
| 2011/0188534 A1 | 8/2011 | Nishimura et al. | |

OTHER PUBLICATIONS

International Search Report and Report for Application No. PCT/US2013/057438, dated Mar. 11, 2014 (10 pages).

Wang, S., et al., Nano-watt stabilized DSC and ITS applications. Journal of Thermal Analysis and Calorimetry, vol. 79, 2005, pp. 605-613.

* cited by examiner

QUASIADIABETIC DIFFERENTIAL SCANNING CALORIMETER

CROSS-REFERENCE TO RELATED APPLICATIONS

This application is the National Stage of International Application No. PCT/US2013/057438, filed Aug. 30, 2013. International Application No. PCT/US2013/057438 claims the benefit of U.S. Provisional Application No. 61/696,488, entitled "Quasiadiabetic Differential Scanning calorimeter," filed Sep. 4, 2012. The entire contents of these applications are expressly incorporated by reference herein.

BACKGROUND

The present invention relates to reducing the errors in the measurement of heat flow rate in a differential scanning calorimeter, i.e., a DSC.

In general a calorimeter may be considered to comprise the measuring system and the enclosure. The measuring system includes the sample, a sample container, if used, and a means to measure the sample temperature $T_s$. The enclosure encloses the measuring system, isolates it from the environment and regulates the temperature of the calorimeter. In prior art systems, the temperature of the enclosure may be designated by the symbol $T_0$. This temperature is controlled in a manner that depends on the operating principle of the calorimeter and the experimental method. The temperature difference between the enclosure and the measuring system $T_0-T_s$ is a measured variable that has been used in different ways depending, mainly, on the operating principle of the calorimeter.

The temperature difference is measured across a thermal resistance between the measuring system and the enclosure. Heat flow within a calorimeter may be described by the equation:

$$C\dot{T}_s = \frac{T_0 - T_s}{R} + W$$

where C is the heat capacity of the sample and its container, if a sample container is used; $\dot{T}_s$ is the rate of change of temperature of the measuring system with respect to time; R is the thermal resistance between the measuring system and the enclosure; and W is the total of all other heat supplied to or removed from the measuring system. W may include the heat absorbed by or released from the sample during a transition, for example the latent heat of fusion, or it may include heat supplied to or removed from the measuring system as required by the operating mode of the instrument, for example, by heaters that supply power to compensate for sample heat effects.

Calorimeters may be divided into two broad categories depending upon how the temperature difference $\Delta T = T_0 - T_s$ is controlled and used. In adiabatic calorimeters $\Delta T=0$, consequently there is no heat exchange between the measuring system and the enclosure. All other calorimeters where $\Delta T \neq 0$ may be classified as nonadiabatic because there is heat exchange between the measuring system and the enclosure. Under this classification system, a heat flux differential scanning calorimeter is a nonadiabatic-nonisothermal calorimeter in which the temperature of the enclosure is controlled to follow a desired temperature program, i.e., $T_0 = T_0(t)$. $\Delta T = \Delta T(t)$, is used as the principal signal in the heat flow rate measurement.

In calorimetry, heat fluxes that occur within the measuring system that are not detected by the heat flow sensor are considered to be heat leakage. Because this heat leakage supplies part of the heat flow between the sample under analysis and the enclosure it may be a measurement error. There are two possibilities for dealing with the problem of heat leakage: adiabatic operation and twin calorimeters.

In adiabatic operation, the temperatures of the measuring system and the calorimeter enclosure are controlled so that they are equal, thereby eliminating heat leakage. In most cases, realization of adiabatic operation requires additional heating or cooling of the measuring system to force $\Delta T$ to be zero. Typically electric resistance heating elements and Peltier devices are used in adiabatic calorimeters to heat or cool the measuring system to maintain adiabatic operation.

In twin calorimeters, two nominally identical measuring systems are installed symmetrically within the calorimetric enclosure. One of the calorimeters contains the sample under analysis and the other contains an inert reference sample or is operated empty. To the extent that the two calorimeters are identical and symmetrically placed, the heat leakage of the two will be identical and subtracting the measured heat flow of the reference calorimeter from the sample calorimeter will cancel the heat leakage and heat exchange effects of the measuring systems, such as heat accumulation. However, the presence of the sample means that the two calorimeters are not in fact identical and so, the heat leakage effects and heat exchange effects within the measuring systems are not completely cancelled.

A heat flux differential scanning calorimeter is a twin calorimeter where the measurement of heat flow rate is obtained from the temperature differences between the two measurement systems and the calorimeter enclosure. To get the sample heat flow rate, the principle of conservation of energy is applied to the calorimetric system and an equation or system of equations describing temperature, heat flows and heat inputs is obtained. The resulting equation or set of equations, subject to some level of simplification is used to find the sample heat flow rate from the measured quantities.

A simplified measurement equation for the heat flux DSC may be obtained by assuming steady-state conditions, i.e., constant heat flow rates; only one thermal resistance, the apparent resistance between the furnace and the sample is taken into account assuming no interaction between the sample and reference. Only the heat capacities of the sample and reference ($C_s$, $C_r$) are taken into account; the other heat capacities are neglected. The sample temperature and measured temperature are assumed equal and there is no heat exchange with the enclosure, i.e., no heat leakage.

The resulting equation is:

$$q = \frac{-\Delta T}{R}$$

where $\Delta T = T_s - T_r$, $T_s$ and $T_r$ are the temperatures of the sample and reference measuring systems and R is the overall thermal resistance between the sample and the enclosure. This equation is widely used in DSCs presently in use today.

U.S. Pat. No. 6,488,406 (the "'406 patent"), which is incorporated by reference herein, describes a method for measuring heat flow rate in a heat flux DSC that avoids many of the assumptions of the simplified method described above. In particular, it does not assume steady-state conditions. It includes the sample and reference calorimeter thermal resistances and the thermal resistances between the sample and reference calorimeters and their respective containers. It also includes sample and reference container and sample and reference calorimeter heat capacities and sample temperature is not assumed to equal the measured temperature. The measured sample heat flow rate is given by:

$$q = q_s - \frac{m_{ps}}{m_{pr}} \frac{\dot{T}_{ss}}{\dot{T}_{rr}} q_r$$

The measured sample and reference calorimeter heat flow rates $q_s$ and $q_r$ are given by:

$$q_s = \frac{\Delta T_0}{R_s} - C_s \dot{T}_s$$

$$q_r = \frac{\Delta T_0 + \Delta T}{R_r} - C_r(\dot{T}_s - \Delta \dot{T})$$

$$\Delta T_0 = T_0 - T_s$$

where $R_s$, $R_r$, $C_s$ and $C_r$ are thermal resistances and heat capacities of the sample and reference calorimeters which are determined by a calibration procedure; $m_{ps}$ and $m_{pr}$ are the masses of the sample and reference containers; and $\dot{T}_{ss}$ and $\dot{T}_{rr}$ are the sample and reference container heating rates.

Sample and reference container temperatures $T_{ss}$ and $T_{rr}$ are given by:

$$T_{ss} = T_s - q_s R_{ss}$$

$$T_{rr} = T_r - q_r R_{rr}$$

where $R_{ss}$ and $R_{rr}$ are the thermal contact resistances between the sample and reference containers and their respective calorimeters. Heat flow sensors disclosed in U.S. Pat. No. 6,431,747 (the "'747 patent") and U.S. Pat. No. 7,470,057 (the "'057 patent"), which are incorporated by reference herein, are suitable for use with this method. These patents disclose means for measuring the two differential temperatures, $\Delta T$ and $\Delta T_0$, required by the method.

U.S. Pat. No. 7,306,365 (the "'365 patent"), U.S. Pat. No. 7,025,497 (the "'497 patent") and U.S. Pat. No. 6,843,595 (the "'595 patent"), which are incorporated by reference herein, disclose heat flux differential scanning calorimeters and heat flow rate measurement methods that include heat leakage in the heat flow rate measurement method. In these disclosures it is assumed that the temperature of the DSC enclosure is uniform in temperature and equal to $T_0$, the temperature at the base of the DSC sensor. The equation for sample heat flow including leakage heat flows is:

$$q = q_s\left(1 + \frac{R_{ss}}{R_{se}}\right) + \frac{\Delta T_0}{R_{se}} - \frac{m_{ps}}{m_{pr}} \frac{\dot{T}_{ss}}{\dot{T}_{rr}} \left(q_r\left(1 + \frac{R_{rr}}{R_{re}}\right) + \frac{\Delta T_0 + \Delta T}{R_{re}}\right)$$

where $R_{se}$, $R_{ss}$ are the thermal resistances between the sample container and the enclosure and between the reference container and the enclosure, i.e., the leakage resistances. This equation is similar in form to the heat flow rate equation of the '406 patent except that it includes two additional terms and two factors multiplying the measured heat flow rates. The second and fourth terms are components of the leakage heat flows between the sample container and the enclosure and between the reference container and the enclosure. The additional factors that multiply the measured sample and reference heat flow rates are each very close to unity because $R_{se}$ is about two orders of magnitude greater than $R_{ss}$ and $R_{re}$ is about two orders of magnitude greater that $R_{rr}$. The measured sample and reference heat flow rates $q_s$ and $q_r$ are the same as in the '406 patent.

SUMMARY

This summary is intended to provide an overview of the subject matter of the present invention, and is not intended to identify essential features or key elements of the subject matter, nor is it intended to be used to determine the scope of the claimed invention. The proper scope of the invention may be ascertained from the detailed description of the embodiments provided below, the figures referenced therein, and the claims.

In the prior art systems described in the background section above, $T_0$ was used for the enclosure temperature, because it was assumed that the enclosure temperature and the terminal temperature of the calorimeter thermal resistances were the same. That use is consistent with the general calorimetric concepts that are discussed above, including adiabatic and twin calorimeter operation, and is consistent with the practice in prior art patents and publications. However, the embodiments of the DCS disclosed herein recognize that there may be a difference between the temperature of the enclosure and the temperature at the base of the DSC sensor. Thus the heat flow calculations set forth below distinguish between the temperature of the enclosure itself, designated as $T_s$, and the temperature at the base of the DSC sensor, $T_0$.

Embodiments of the differential scanning calorimeter are directed toward reducing the errors in the measurement of heat flow rate in a heat flux differential scanning calorimeter by addressing heat leakage within the calorimeter in two ways. The first is by operating in a quasiadiabatic mode wherein the majority of the heat leakage is suppressed. The second is by applying a heat flow rate measurement algorithm that includes the leakage heat flow rate to determine the heat flow balance within the differential scanning calorimeter.

Embodiments of the differential scanning calorimeter ("DSC") are directed towards a DSC employing the heat flux measurement principle that reduces the error in measured heat flux due to heat leakage. They include means for heating, cooling and controlling the temperature of the DSC enclosure independently of the temperature of the measuring system. This allows the temperature difference between the sample and reference containers and the enclosure to be minimized thereby minimizing the leakage heat flows. In addition, they include a heat flow rate measurement method that accounts for the remaining heat leakage, further decreasing the heat flow rate errors due to heat leakage. In these embodiments, the temperature of the enclosure is measured independently of the temperature of the measuring system.

Embodiments include a method of measuring heat flow in a differential scanning calorimeter having a measuring system and an enclosure. The method includes controlling a temperature of the measuring system. The method also includes controlling a temperature of the enclosure independently of the temperature of the measuring system, and then determining the differential heat flow to a sample container of the differential scanning calorimeter compared to a reference container of the differential scanning calorimeter.

Embodiments of the differential scanning calorimeter may include DSCs that use a method of measuring a differential heat flow in a differential scanning calorimeter. The differential scanning calorimeter may include a block of high thermal conductivity material within an enclosure. The block of high thermal conductivity material in turn includes a sample measuring system and a reference measuring system, includes a thermocouple for measuring the temperature of the enclosure, and includes a temperature controller for controlling the temperature of the block of high thermal conductivity material according to a predetermined temperature program. It also includes a thermocouple configuration for measuring $T_0$, $\Delta T$, $\Delta T_0$, and $T_0$, where $T_0$ is the temperature of the block of high thermal conductivity material, $\Delta T$ is the difference between the temperature of the sample measuring system and the temperature of the reference measuring system, $\Delta T_0$ is the difference between the temperature of the block of high thermal conductivity material and the temperature of the sample measuring system, and $T_e$ is the temperature of the enclosure. The system also includes modules with a computer for calculating the temperature of a sample container in the sample measuring system and the temperature of a reference container in the reference measuring system based upon the measured values of $T_0$, $\Delta T$ and $\Delta T_0$. It further includes a temperature controller for controlling the temperature of the enclosure to follow a weighted average of the calculated temperature of the sample container and the calculated temperature of the reference container. The computer system includes a module for calculating a differential heat flow to the sample container with respect to a heat flow to the reference container based upon measuring $\Delta T$, $\Delta T_0$, $T_0$ and $T_e$ by using an algorithm that comprises corrections to the measured heat flow to the sample container based in part upon the difference between the temperature of the enclosure and the temperature of the sample container.

Other structures, objects, features and advantages of embodiments of the present invention will be apparent to one of ordinary skill in the art upon examination and study of the following detailed description and the accompanying figures. It is intended that all such additional structures, features and advantages of the invention be included within this description and this summary, be within the scope of the embodiments and be protected by the claims set forth below.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS OF THE INVENTION

For clarity, the detailed descriptions herein describe certain exemplary embodiments, but the disclosure herein may be applied to any differential scanning calorimeter comprising certain of the features described herein and recited in the claims.

Figure 1:
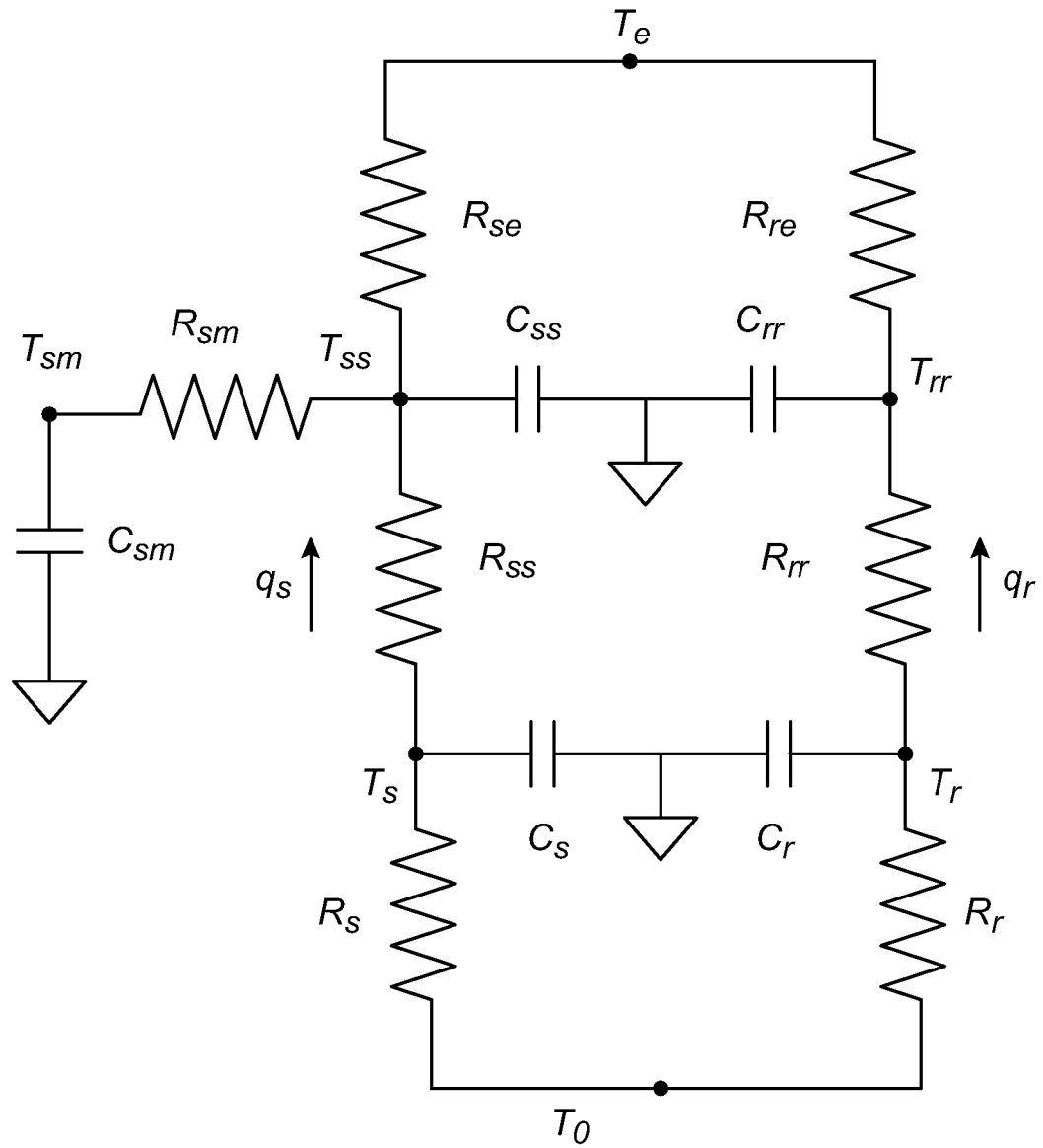
FIG. 1 is a schematic diagram of a thermal network model according to an embodiment of the differential scanning calorimeter.

FIG. 1 is a lumped heat capacity thermal network model of an embodiment of a DSC including the leakage heat flows. The leakage thermal resistances $R_{se}$ and $R_{re}$ are connected to the enclosure temperature $T_e$ (not to $T_0$) and a separate sample is included in the network model having temperature $T_{sm}$ and heat capacity $C_{sm}$. In the network model, the sample is coupled to the sample container by a contact thermal resistance $R_{sm}$. The sample is not needed to perform the heat flow balance and find the sample heat flow, but is included to facilitate the study of heat flow error due to heat leakage.

Assuming that both $T_n$ and $T_e$ heat at constant rate b, but that their temperatures differ by a fixed offset and that no transitions or reactions occur in the sample, once steady state is achieved, all other temperatures also heat at the rate b. This condition corresponds to what is commonly referred to as the heat flow baseline and is the portion of the DSC result that may be used to evaluate the sample heat capacity. Solutions for the temperatures are substituted into the heat flow measurement equations of the '406 patent set forth above to give the measured result equation:

$$q_m = (T_0 - T_e)\left(\frac{1}{R_{ss} + R_s + R_{se}} - \frac{1}{R_{rr} + R_r + R_{re}}\right) +$$
$$b\left(\frac{(C_{ss} + C_{sm})R_{se}}{R_{ss} + R_s + R_{se}} - \frac{C_{rr}R_{re}}{R_{rr} + R_r + R_{re}}\right) +$$
$$b\left(\frac{C_r R_r}{R_{rr} + R_r + R_{re}} - \frac{C_s R_s}{R_{ss} + R_s + R_{se}}\right)$$

This is not a measurement equation because it does not include the measured variables; rather it is a result equation that shows what the measurement actually includes. The first term is proportional to the difference between the sensor base temperature and the enclosure temperature. It is the difference between the heat that flows through each of the two measuring systems between $T_0$ and $T_e$. The second term represents the difference between the heat stored in the sample and its container and the heat stored in the reference container. The third term includes the difference in heat storage between the sample and reference measuring system. Of these three terms, only the second includes the sample heat capacity.

In the absence of heat leakage, the leakage thermal resistances $R_{se}$ and $R_{re}$ would be essentially infinite. Consequently, the denominators of the first and third terms would become essentially infinite, making those two terms zero. The resistance ratios in the second term would become one and the resulting measured heat flow rate would be:

$$q_m = b(C_{ss} + C_{sm} - C_{rr}).$$

This is the exact result when the sample and reference containers have the same mass, i.e., $C_{ss} = C_{rr}$. This result shows that heat flow rate measurement errors, at least when measuring heat capacity, are the direct result of heat leakage because if the leakage existed, the measured heat flow rate would not correspond to that required by the sample heat capacity.

If the sample and reference calorimeters are perfectly symmetrical. i.e., the thermal resistances and heat capacities in the sample and reference calorimeters match exactly, the first and third terms are zero and the result of the measurement is:

$$q_m = \frac{bC_{sm}R_{se}}{R_{ss} + R_s + R_{se}}$$

The correct or true heat flow rate is:

$$q_t = bC_{sm}$$

The calibration factor is the ratio of the true to the measured heat flow rates. In the case of the perfectly symmetrical DSC it is:

$$K = \frac{R_{ss} + R_s + R_{se}}{R_{se}}.$$

The calibration factor is independent of the sample heat capacity and the measured heat flow rate.

However, calorimeters are generally not perfectly symmetrical. In those cases, the first and third terms are not zero. Moreover, they do not include the measured heat flow are and are not proportional to the true heat flow, making the calibration factor dependent on the sample heat capacity, which might introduce errors. To show this, the equation for the measured heat flow can be simplified. The first and third terms are assumed to be constant because they include only instrument coefficients, the heating rate b and the temperature difference $T_0-T_s$. Assume that the sample and reference container heat capacities are equal and that the resistance ratios in the second term are equal. The measured result equation becomes:

$$q_m = L + Mq_t + N$$

where $$L = (T_0 - T_e)\left(\frac{1}{R_{ss} + R_s + R_{se}} - \frac{1}{R_{rr} + R_r + R_{re}}\right);$$

$$M = \frac{R_{se}}{R_{ss} + R_s + R_{se}}; \text{ and}$$

$$N = b\left(\frac{C_r R_r}{R_{rr} + R_r + R_{re}} - \frac{C_s R_s}{R_{ss} + R_s + R_{se}}\right).$$

Assume that in a first experiment, the true heat flow is $q_t$ and in a second experiment, the true heat flow is $q_t/2$. The calibration factors for the two experiments become:

$$K_1 = \frac{q_t}{L + Mq_t + N}$$

$$K_2 = \frac{q_t}{2L + Mq_t + 2N}$$

The two correction factors are different; if we perform a heat flow calibration experiment for a given sample heat capacity, it will only be correct for another sample that has the same heat capacity. This is the direct result of heat flow leakage because, as shown above, if the leakage did not exist, the heat flow measurement would only include the second term and heat flow calibration would not depend on the sample heat flow rate.

FIG. 1 is a lumped heat capacity thermal network model representing the measuring system with boundary node $T_0$ that represents the temperature at the base of the DSC sensor that is used to control the measurement assembly temperature, and boundary node $T_e$ that represents the enclosure temperature. The measured heat flow rate including heat leakage to the enclosure at $T_e$ is obtained as follows:

$$q = q_s + \frac{T_e - T_{ss}}{R_{se}} - \frac{m_{ps}}{m_{pr}} \frac{\dot{T}_{ss}}{\dot{T}_{rr}} \left(q_r + \frac{T_e - T_{rr}}{R_{re}}\right)$$

This heat flow rate equation includes a leakage term added to each of the measured sample and reference heat flow rates. These terms are the heat that is exchanged between the sample container and the enclosure and between the reference container and the enclosure. It differs from the equations of the '365, '497 and '595 patents in that the factors multiplying $q_s$ and $q_r$ do not appear and the temperature differences in the numerators of the leakage terms are $T_e-T_{ss}$ and $T_e-T_{rr}$.

In operation, the temperature $T_0$ shown in the thermal network of FIG. 1 is controlled to follow the desired thermal program, typically comprising constant temperature and constant heating rate segments. When the DSC is heated at a constant rate such that both $T_0$ and $T_e$ heat at the same rate but are offset from one another. $T_e$ may lag behind $T_0$. During steady state, calorimeter temperatures $T_s$ and $T_{rr}$ container temperatures $T_{ss}$ and $T_{rr}$ and sample temperature $T_{sm}$ will also heat at the same heating rate but with different offsets, i.e., different temperature lags relative to $T_0$. The leakage thermal resistances $R_{se}$ and $R_{rn}$ are generally much greater than the other thermal resistances within the system. Typically they are one to two orders of magnitude greater. Heat will flow from $T_0$ through each calorimeter to each of the sample and reference containers. At the same time, heat will be exchanged between each of the sample and reference containers and the enclosure at temperature $T_s$. The heat that flows through the sample and reference calorimeters to each of the containers through contact resistances $R_{ss}$ and $R_{rr}$ are the measured heat flow rates $q_s$ and $q_r$. The total heat that flows to the sample container is the sum of the heat that flows to it through its calorimeter, which is the measured sample heat flow, the heat that flows through its leakage resistance and the heat exchanged between it and the sample. The total heat that flows to the reference container is the sum of the heat that flows to it through its calorimeter, which is the measured reference heat flow, and the heat that flows through its leakage resistance.

Depending upon the temperature of the enclosure $T_e$ relative to the container temperatures, heat may flow into or out of the container through the leakage resistance. When $T_e$ is lower than the container temperature, heat flows from the container to $T_e$. This heat loss from the container must be made up by heat flowing to the container through the calorimeter, thus making the measured heat flow too large. Conversely, when $T_e$ is higher than the container temperature, heat flows into the container through the leakage resistance reducing the heat flow to the container through the calorimeter, making the measured heat flow lower than the actual heat flow to the container. If the sample and reference calorimeters, containers and samples were perfectly symmetrical, the errors in the measured heat flows in both the sample and reference calorimeters would be equal and would cancel. It can be seen that the above heat flow measurement equation corrects this situation by either adding the leakage heat flow to or subtracting the leakage heat flow from the measured heat flow to each container depending on whether $T_e$ is below or above the container temperature. To implement this measurement method requires that the temperature of the enclosure $T_e$ be measured and that the values for leakage thermal resistances be known.

To apply this heat flow measurement method, the calorimeter thermal resistances and heat capacities must be determined by a calibration method. This calibration method uses two identical constant heating rate experiments but uses empty containers in one experiment, and uses containers of the same type with samples of known heat capacity in the second experiment. Examples of materials that may be used as samples in the second experiment include sapphire samples having a mass of about 65 mg. Typically the same material is used for both samples in the second experiment, with masses that match within a few mg. Other materials may be used in the second experiment, as long as they do not have any transitions in the temperature range of interest, and have a heat capacity that is known with sufficient precision. The reason for including containers in these calibration experiments is that the leakage resistances are dependent on whether and what type of containers are present. With this configuration, the same leakage resistances are present in both calibration experiments.

The calorimeter thermal resistances and heat capacities $R_s$, $R_r$, $C_s$, $C_r$ are determined as follows. First, heat balance equations are written for temperature nodes $T_s$, $T_{ss}$, $T_r$ and $T_{rr}$ of the thermal model in FIG. 1 for each of the calibration experiments. The heat capacities of the samples are added to those of the container for the experiment that includes samples. Then the pair of equations for $T_s$ and $T_{ss}$ are solved for $R_s$ and $C_s$ in terms of the measured and known quantities and the equations for $T_r$ and $T_{rr}$ are solved for $R_r$ and $C_r$ in terms of the measured and known quantities.

The measured quantities are: $\Delta T$, $\Delta T_0$, $T_s$ and $T_e$. The known quantities are the heat capacities of the containers and the samples, the thermal contact resistances between the containers and calorimeters and the leakage thermal resistances. The resulting equations are:

$$R_s = \frac{(\Delta T_{01} - \Delta T_{02})(R_{se} + R_{ss})}{bR_{se}(C_{ss1} - C_{ss2}) + T_{e2} - T_{s2} - T_{e1} + T_{s1}}$$

$$C_s = \frac{\Delta T_{01}(T_{e2} - T_{s2} - bR_{se}C_{ss2}) + \Delta T_{02}(bR_{se}C_{ss1} - T_{e1} + T_{s1})}{b(\Delta T_{01} - \Delta T_{02})(R_{se} + R_{ss})}$$

$$R_r = \frac{(\Delta T_{01} + \Delta T_1 - \Delta T_{02} - \Delta T_2)(R_{re} + R_{ss})}{bR_{re}(C_{rr1} - C_{rr2}) + \Delta T_2 - \Delta T_1 + T_{e2} - T_{s2} - T_{e1} + T_{s1}}$$

$$C_r = \frac{(\Delta T_{01} + \Delta T_1)\begin{pmatrix} T_{e2} - T_{s2} + \\ \Delta T_2 - bR_{re}C_{rr2} \end{pmatrix} - (\Delta T_{02} + \Delta T_2)\begin{pmatrix} T_{e1} - T_{s1} + \\ \Delta T_1 - \\ bR_{re}C_{rr1} \end{pmatrix}}{b(\Delta T_{01} + \Delta T_1 - \Delta T_{02} - \Delta T_2)(R_{re} + R_{rr})}$$

The subscripts 1 and 2 indicate the first and second of the calibration experiments. Heat capacities $C_{ss}$ and $C_{rr}$ are the heat capacities of the empty containers in the first experiment and the sum of the heat capacities of the container plus the sample for the experiment with samples in the second experiment. If, during the calibration experiments. $T_e = T_s$, the calibration equations may be simplified. As shown below, the structure of the DSC allows the DSC to be operated in that manner, simplifying the equations. The sample calorimeter thermal resistance $R_s$, the sample calorimeter heat capacity $C_s$, the reference calorimeter thermal resistance $R_r$, and the reference calorimeter heat capacity $C_r$ are given by the following expressions:

$$R_s = \frac{(\Delta T_{01} - \Delta T_{02})(R_{se} + R_{ss})}{bR_{se}(C_{ss1} - C_{ss2})}$$

$$C_s = \frac{R_{se}(\Delta T_{02}C_{ss1} - \Delta T_{01}C_{ss2})}{(\Delta T_{01} - \Delta T_{02})(R_{se} + R_{ss})}$$

$$R_r = \frac{(\Delta T_{01} + \Delta T_1 - \Delta T_{02} - \Delta T_2)(R_{re} + R_{ss})}{bR_{re}(C_{rr1} - C_{rr2}) + \Delta T_2 - \Delta T_1}$$

$$C_r = \frac{(\Delta T_{01} + \Delta T_1)(\Delta T_2 - bR_{re}C_{rr2}) - (\Delta T_{02} + \Delta T_2)(\Delta T_1 - bR_{re}C_{rr1})}{b(\Delta T_{01} + \Delta T_1 - \Delta T_{02} - \Delta T_2)(R_{re} + R_{rr})}$$

Figure 2:
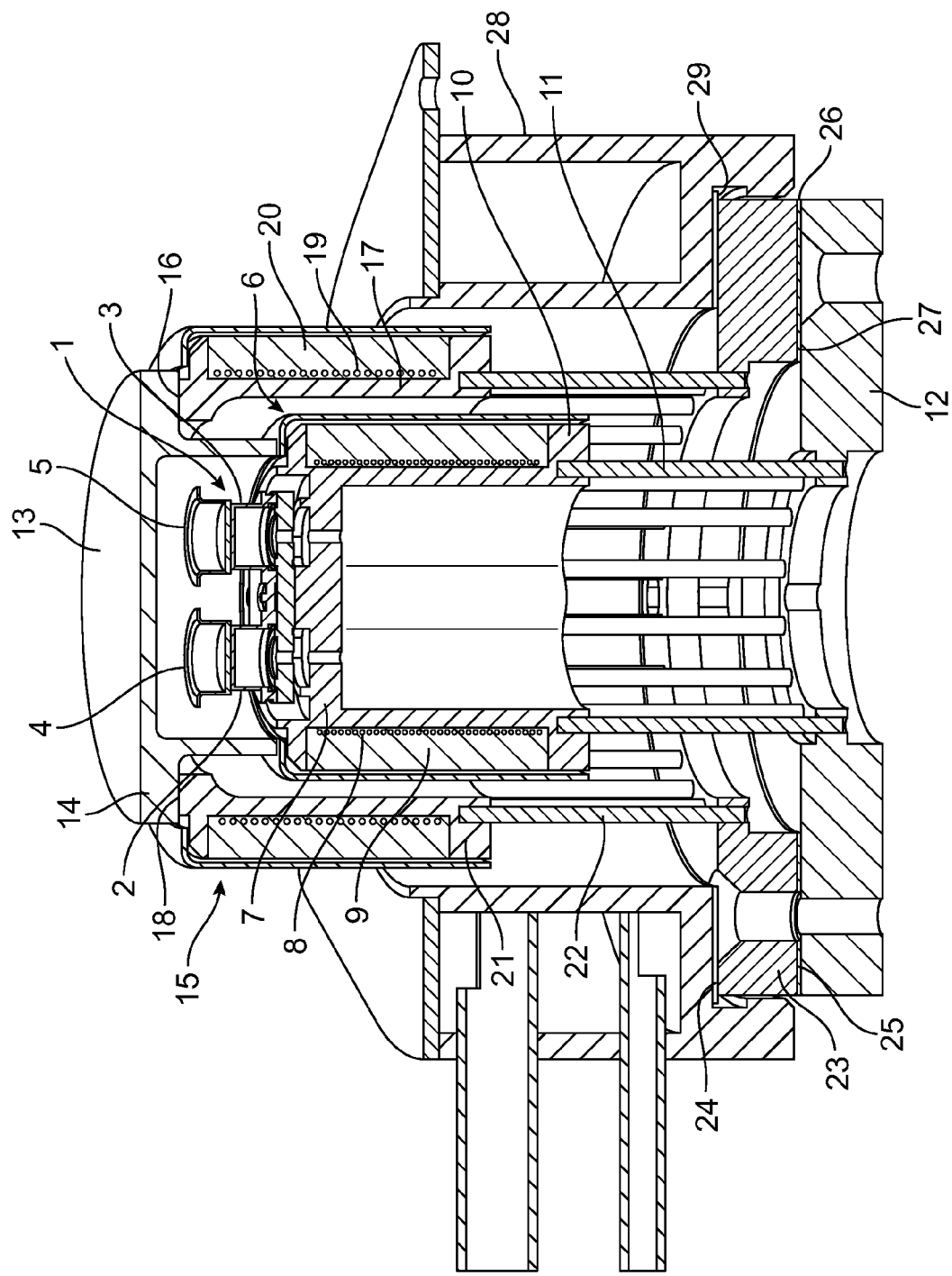
FIG. 2 is a schematic diagram of a cross-section of an embodiment of the differential scanning calorimeter.

FIG. 2 is a vertical cross section of an exemplary embodiment taken through the plane intersecting the vertical axes of the sample and reference calorimeters. In this embodiment, heat flow sensor 1 has sample and reference positions 2 and 3, respectively, with sample and reference containers 4 and 5 installed on the sample and reference positions, respectively. The sensor assembly may be joined to the measurement heating/cooling assembly 6 by a method such as brazing that ensures a highly reproducible, high thermal conductivity connection between the sensor and the measurement heating/cooling assembly.

In this exemplary embodiment, the measurement heating assembly 6 comprises a base structure 7, manufactured from a high thermal conductivity material such as silver, gold, copper or aluminum in the form of a hollow cylinder with one end closed. Platinum alloys or ceramic materials could be used for high temperature measurements. The heat flow sensor may be attached to the closed end of the base structure and a heating element 8 may be wound on the outer cylindrical surface 9 of the base structure. The open end of the base structure may comprise a flange 10 to which may be joined a number of thermal resistors 11 in the form of slender cylindrical rods. The opposite ends of the rods are joined to a cooling flange 12 in the form a flat circular disk with a hole through the center. This overall structure provides means for heating and cooling and for regulation of the temperature of the DSC sensor.

The DSC sensor may be enclosed by the dosed-end hollow cylinder 13 that forms the calorimeter enclosure and is essentially uniform in temperature. It is constructed of high thermal conductivity material, for example silver, to maximize its temperature uniformity. It is heated via a relatively thick flange 14 that is integral to the enclosure and is positioned close to the junction of the cylindrical wall and the flat bottom of the cylinder that forms the top of the enclosure. The location of the flange may be chosen to make the maximum temperature differences along the cylindrical wall and across the flat top of the enclosure very nearly the same, thereby minimizing the temperature variation within the enclosure and approaching the isothermal condition as closely as possible.

In the exemplary embodiment shown in FIG. 2, flange 14 contacts and exchanges heat with enclosure heating/cooling assembly 15 at flat surface 16. Enclosure heating/cooling assembly 15 comprises a high thermal conductivity, typically silver, open ended hollow cylindrical base structure 17. Flat top surface 18 supports the enclosure and exchanges heat with it via surface 16 of flange 14 of the enclosure. A heating element 19 is wound on the outer cylindrical surface 20 of the base structure. The end of the base structure opposite surface 18 comprises a flange 21 to which are joined a number of thermal resistors 22 in the form of slender cylindrical rods. The opposite ends of the rods are joined to a cooling flange 23 in the form a flat circular disk with a hole through the center. This overall structure provides means for heating, cooling and regulation of the temperature of the DSC enclosure.

In the exemplary embodiment shown in FIG. 2, cooling flange 23 of the enclosure heating/cooling assembly has upper heat exchange surface 24 that is the flat top surface of cooling flange 23 and lower heat exchange surface 25 that is the flat bottom surface of cooling flange 23. Lower heat exchange surface 25 contacts a heat transfer interface material in the form of a thin flat ring 26. It, in turn, contacts heat exchange surface 27 that is the upper flat surface of cooling flange 12 of the measurement heating/cooling assembly. Thus cooling flanges 12 and 23 are connected thermally and exchange heat with each other.

In the exemplary embodiment of FIG. 2, upper heat exchange surface 24 of enclosure cooling flange 23 exchanges heat with cooling device 28 via a thin flat annular thermal interface material 29. Cooling device 28 may be one of a number of devices including the evaporator of a mechanical cooling system, the evaporator of a cooling system using an expendable cryogenic liquid such as liquid nitrogen as exemplified in U.S. Pat. No. 6,578,367, which is incorporated herein by reference; a convection heat exchanger in which a cold fluid like cold water or other liquid flows; an air-cooled heat sink; a thermoelectric cooler; or other types of cooling devices. In this embodiment, the cooling device is the heat sink for the entire system. It provides cooling for the DSC sensor via measuring assembly base structure 7, thermal resistors 11, measuring assembly cooling flange 12 and enclosure cooling flange 23. In a similar manner, it provides cooling for the DSC enclosure via enclosure heating/cooling assembly base structure 17, thermal resistors 22 and cooling flange 23.

Output signals from the measuring assembly, $q_s$, $q_r$, $T_{ss}$, $T_{rr}$ and $T_e$ are used to calculate the sample heat flow using the equation:

$$q = q_s + \frac{T_e - T_{ss}}{R_{se}} - \frac{m_{ps}}{m_{pr}} \frac{\dot{T}_{ss}}{\dot{T}_{rr}} \left( q_r + \frac{T_e - T_{rr}}{R_{re}} \right)$$

Although in principle the measurement can be made as written, the numerators of the leakage terms involve temperature differences that will be quite small, much less than 1° C. for quasiadiabatic operation. Taking the differences between the values of $T_e$, $T_{ss}$ and $T_{rr}$ to get those temperature differences can introduce significant uncertainty because the temperature differences are taken between large numbers, on the order of hundreds of degrees, to find temperature differences of the order of a few hundredths or thousandths of a degree. This would require that the temperatures $T_e$, $T_{ss}$ and $T_{rr}$ be measured to a very high precision, which is impractical. This can be avoided by substituting the equations given above for $T_{ss}$ and $T_{rr}$. The resulting equation for heat flow rate is:

$$q = q_s\left(1 + \frac{R_{ss}}{R_{se}}\right) + \frac{T_e - T_s}{R_{se}} - \frac{m_{ps}}{m_{pr}} \frac{\dot{T}_{ss}}{\dot{T}_{rr}}\left(q_r\left(1 + \frac{R_{rr}}{R_{re}}\right) + \frac{T_e - T_s + \Delta T}{R_{re}}\right)$$

Algebraic equivalents to the above equation, i.e., equations for q that give the same result but may use somewhat different formulations for the factors in the equation, may be used instead of the above equation. For example, the equation could replace $T_e - T_s + \Delta T$ with $T_e - T_r$, since $\Delta T = T_s - T_r$. Other possible expressions could also be used in the equation for heat flow rate, such as $T_e - T_r - \Delta T$ or $T_e - T_0 - \Delta T_0$. Additional expressions for calculating temperatures and temperature differences are disclosed in the '747 patent. Heat flow rate equations that use any variation of the above equation to calculate the heat flow rate and provide the same result are algebraically equivalent to the equation set forth above.

Figure 3:
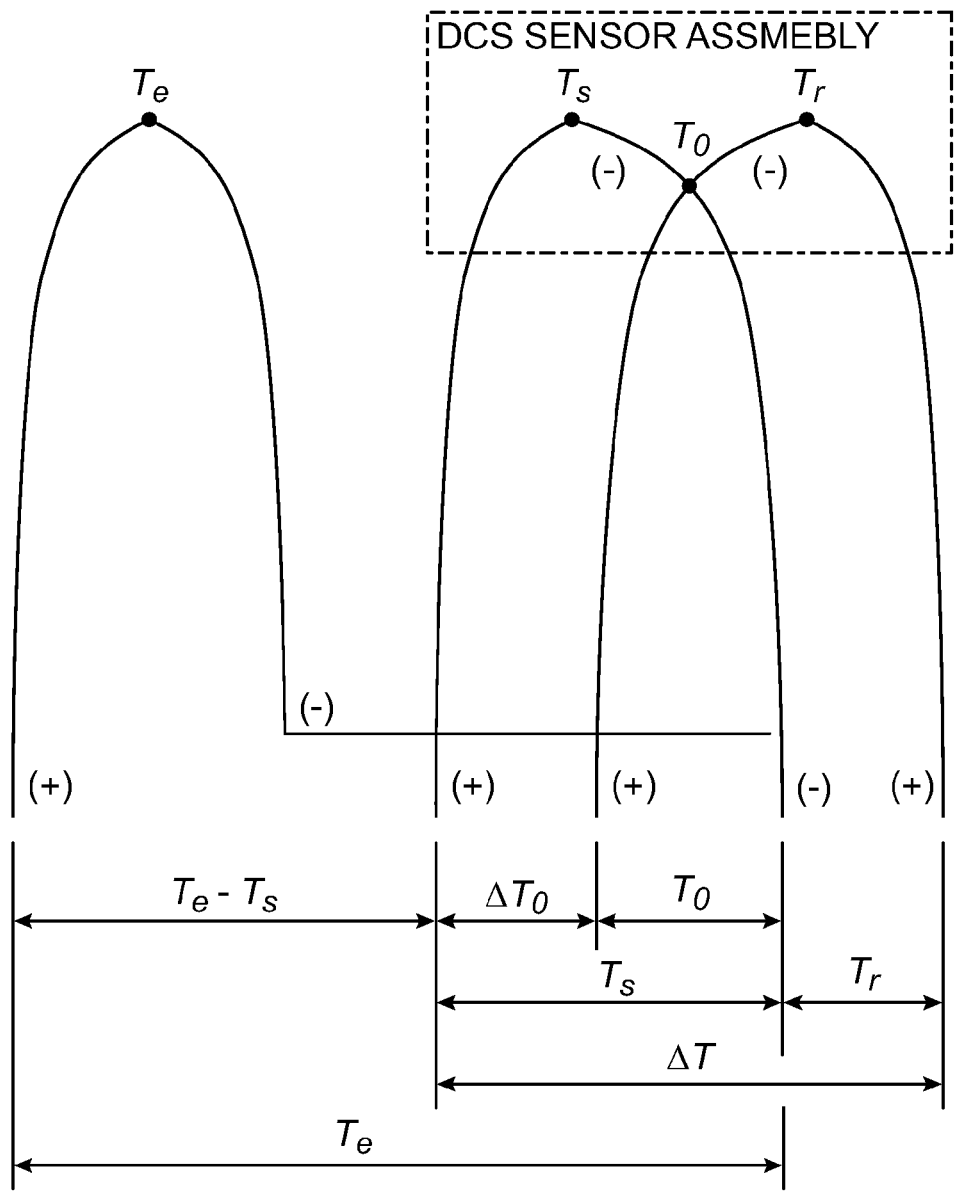
FIG. 3 is a schematic of a thermocouple configuration that may be used in the differential scanning calorimeter shown in FIG. 2.

Calculating q thus requires measurement, for example, of the temperature difference $T_e - T_s$ which may be done as indicated in the temperature measurement schematic of FIG. 3. FIG. 3 is a schematic diagram showing the configuration of the thermocouples used in the exemplary DSC of FIG. 2. It comprises the DSC sensor thermocouples with the enclosure thermocouple added. Nodes $T_s$, $T_r$ and $T_0$ represent thermocouples junctions that are part of the DSC sensor assemblies described in the '747 and '057 patents. The (+) and (−) signs indicate the polarity of the thermocouple conductors. Temperature $T_0$ is measured between the positive and negative conductors connected to the $T_0$ junction, the temperature difference $\Delta T_0$ is measured between the positive conductors connected to the $T_0$ and $T_s$ junctions and the temperature difference $\Delta T$ is measured between the positive conductors connected to the $T_s$ and $T_r$ junctions.

As shown in FIG. 3, the DSC also includes a thermocouple to measure $T_e$. The negative wire of the $T_e$ thermocouple is connected to the negative wire of the $T_0$ thermocouple, facilitating the measurement of temperature difference $T_e - T_s$ between the positive conductors connected to the $T_e$ and $T_s$ thermocouple junctions as required in the above heat flow equation. This temperature difference can be readily measured with the requisite precision.

While $T_s$ and $T_r$ may be measured directly between the positive conductors connected to their respective junctions and the negative conductor connected to the $T_0$ thermocouple junction, in practice they may be obtained by summing the voltages corresponding to $T_0$, $\Delta T_0$ and $\Delta T$ according to the definitions of the temperature differences $\Delta T_0$ and $\Delta T$. Thus $T_s = T_0 - \Delta T_0$ and $T_r = T_s - \Delta T$ which is equivalent to measuring the temperatures directly.

Thermocouple junction $T_e$ may be attached to the removable cover comprising the DSC enclosure. Its negative conductor is connected to the negative conductor of the $T_0$ thermocouple allowing the temperature difference $T_e - T_s$ to be measured between the positive conductors of the $T_e$ and $T_s$ thermocouples. This method of connecting the four thermocouples allows the temperature differences $\Delta T$, $\Delta T$ and $T_e - T_s$ to be measured with high precision as required by the heat flow rate measurement while making all temperatures available.

Figure 4:
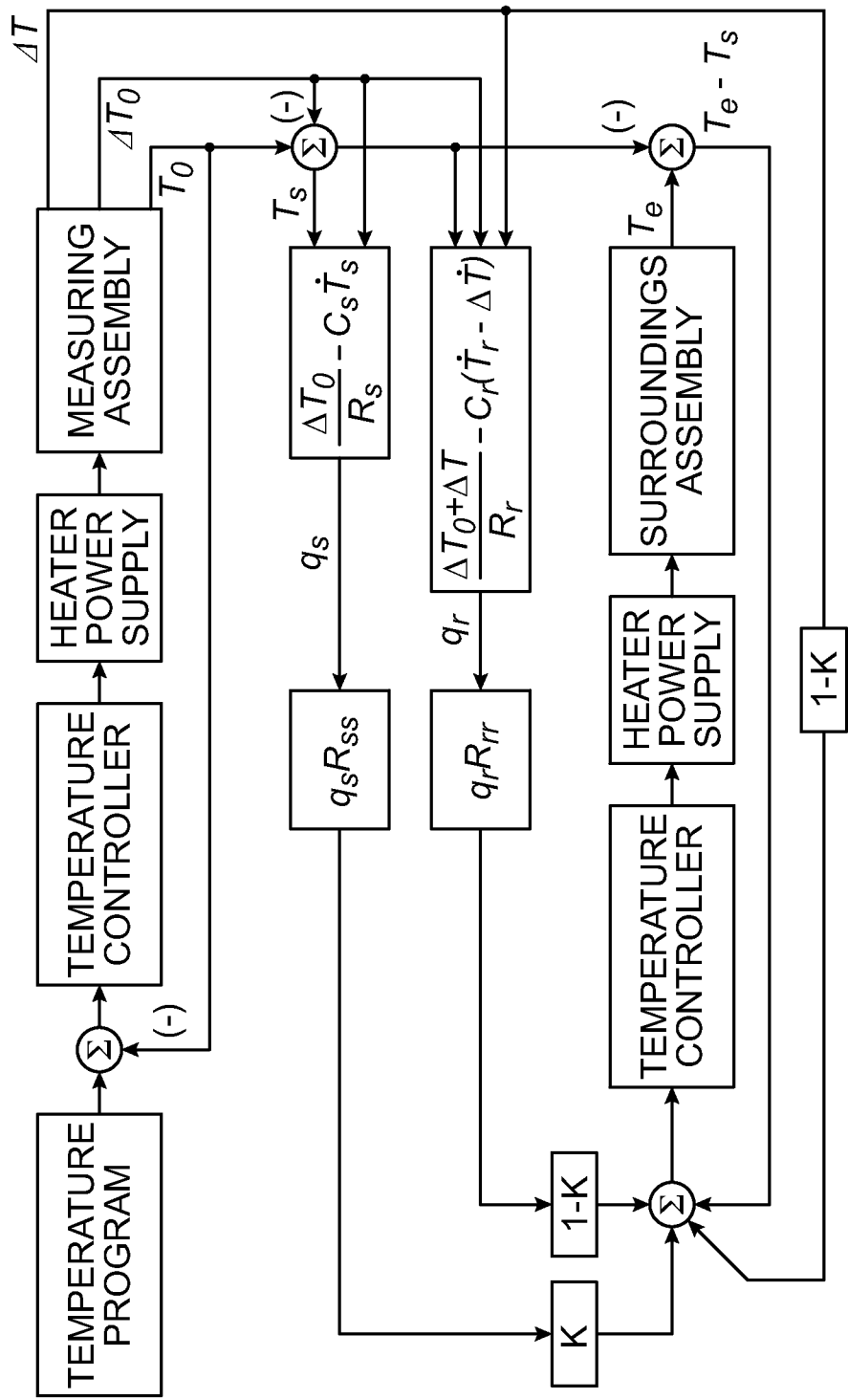
FIG. 4 is a block diagram of a temperature control system that could be used with the embodiment of FIG. 2.

FIG. 4 is a block diagram of an exemplary temperature control system that may be used in the exemplary embodiment shown in FIG. 2. The temperature program defines the desired trajectory of temperature versus time of the DSC for the desired experiment. It comprises constant temperature segments of defined duration, constant heating/cooling rate segments that typically are defined by terminal temperatures and the rate of change of temperature with respect to time, periodic temperature oscillations for a modulated temperature DSC experiment and other experimental segment types depending upon the material property or phenomenon under investigation and the desired temperature range of the experiment. The temperature program is the temperature set point for the measuring assembly temperature control system. It is used to control $T_0$, the temperature of the base of the DSC sensor.

The DSC sensor base temperature $T_0$ is subtracted from the set point temperature to create the temperature error signal which is input to the temperature controller. The temperature controller may employ any of a number of well-known control algorithms, for example the well-known proportional plus integral plus derivative algorithm, that operate on the error signal to generate a power command that is input to the heater power supply that supplies the desired electrical current to the heating element of the measuring assembly.

Output signals from the measuring assembly are $T_0$, $\Delta T_0$ and $\Delta T$, where $T_0$ is the temperature at the base of the DSC sensor that is used to control the measurement assembly temperature, i.e., it is the temperature of the block of high thermal conductivity material. In operation $T_0$ is controlled to follow the desired temperature program. $\Delta T_0$ is $T_0-T_s$ and $\Delta T$ is $T_s-T_r$. Sample calorimeter temperature $T_s$ is obtained by subtracting $\Delta T_0$ from $T_0$. Measured sample heat flow rate $q_s$ is obtained from $\Delta T_0$ and $T_s$ using the sample heat flow rate measurement equation, while measured reference heat flow rate $q_r$ is obtained from $\Delta T_0$, $\Delta T$ and $T_s$ using the reference heat flow rate measurement equation.

The input for the enclosure temperature control system is the difference between the enclosure temperature $T_e$ and a weighted sum of the sample and reference container temperatures $T_{ss}$ and $T_{rr}$, i.e., $T_e-(KT_{ss}+(1-K)T_{rr})$. Sample container temperature $T_{ss}$ is multiplied by weighting factor K and reference container temperature $T_{rr}$ is multiplied by weighting factor 1-K where, $0 \leq K \leq 1$. When K=0.5, the input is the difference between the enclosure temperature and the straight average of the sample and reference container temperatures; this input is used during heat flow rate measurement. Other values of the weighting factor K may be used if it is advantageous to do so. Because container temperatures are not measured, $T_e-(KT_{ss}+(1-K)T_{rr})$ must be calculated by combining the available inputs. Substituting the equations given above for $T_{ss}$ and $T_{rr}$ into the control input equation and collecting terms gives: $T_e-T_s+Kq_sR_{ss}+(1-K)q_rR_{rr}-(1-K)\Delta T$ which is the input to the temperature controller. During calibration of the DSC, the instrument uses the temperature difference $T_e-T_s$ directly as the input to the temperature controller for the enclosure temperature controller.

The temperature controller may employ any of a number of well-known algorithms, for example proportional plus integral plus derivative, that operate on the error signal to generate a power command that is fed to the heater power supply that supplies the desired electrical current to the heating element of the enclosure assembly. This control system, when used with the embodiment of the DSC structure described in FIG. 2, results in a DSC in which the measuring assembly follows the desired experimental temperature profile while the enclosure assembly follows the weighted average, typically a straight average with K=0.5, of the sample and reference containers resulting in quasiadiabatic operation that minimizes the sample and reference calorimeter leakage heat flows.

Figure 5:
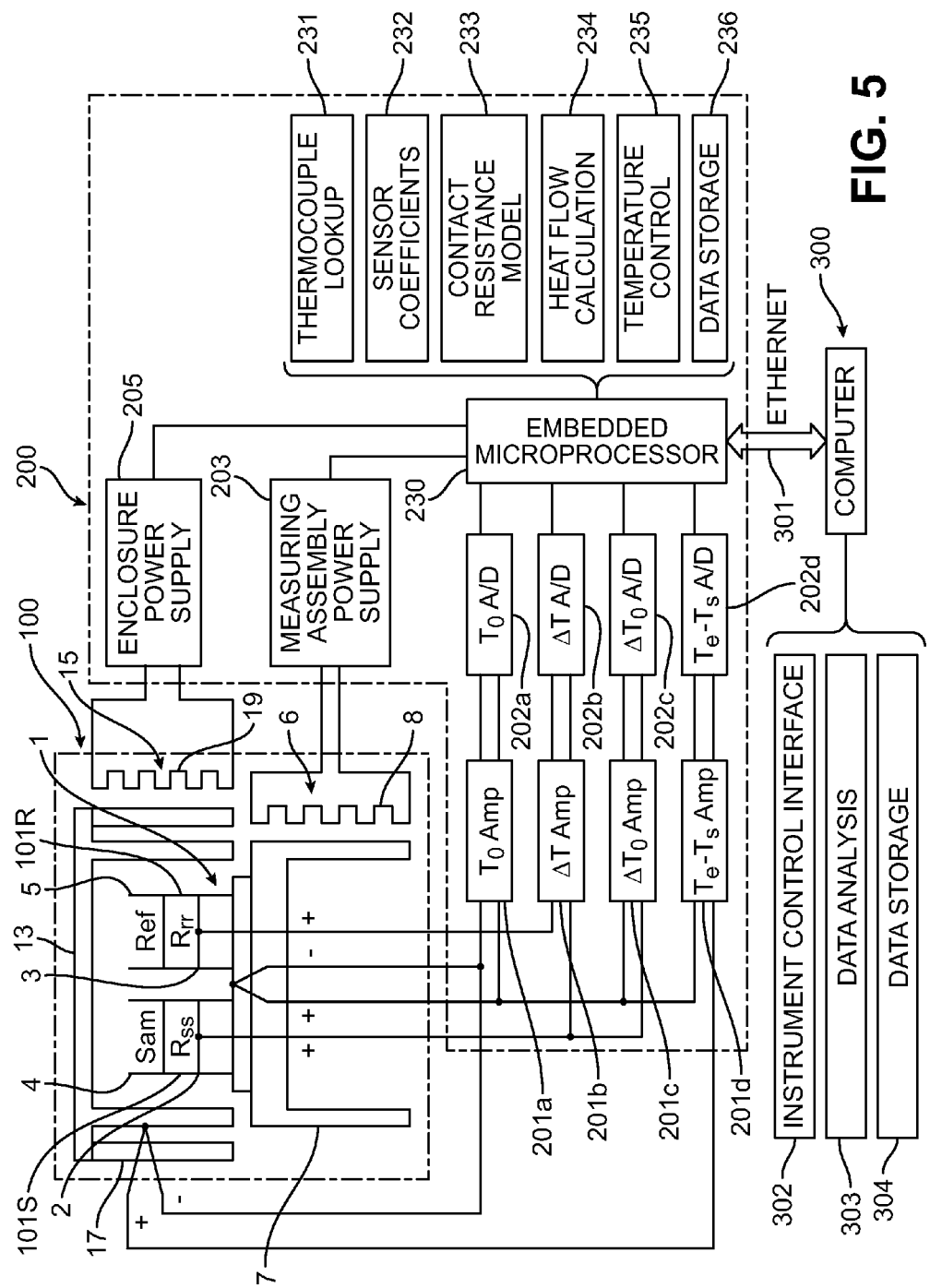
FIG. 5 is a schematic block diagram showing a system for controlling the embodiment of the calorimeter shown in FIG. 2.

FIG. 5 is a schematic diagram of an exemplary system for controlling the embodiment of the calorimeter shown in FIG. 2 and for calculating the heat flows and calibration factors. In the embodiment illustrated in FIG. 5, the DSC comprises three main components: a DSC cell 100, a DSC module 200 and a computer 300, DSC cell 100 comprises a heat flow sensor assembly 1 with a sample position 2 and a reference position 3. A sample within a sample container 4 and a reference sample within a reference container 5 are placed on the sample and reference positions. In alternative cases, the reference container remains empty. Heat is exchanged between each of the containers and its sensor position by a sample thermal contact resistance 101S and a reference thermal contact resistance 101R. Sensor assembly 1 is mounted on base structure 7 of the measurement heating assembly 6 which is heated by heating element 8. The temperature of the measuring assembly is controlled by heating element 8 which is supplied by measuring assembly power supply 203 in response to temperature control function 235 that is executed in embedded microprocessor 230. The output from $T_0$ thermocouple analog to digital converter 202a is controlled to match the desired temperature program. The enclosure, closed-end hollow cylinder 13, is heated by contact with enclosure heating assembly 15 which comprises high thermal conductivity base structure 17 that is heated by heating element 19 which is supplied by enclosure power supply 205 in response to temperature control function 235 that is executed in embedded microprocessor 230. The output from differential thermocouple $T_e-T_s$ analog to digital convertor 202d is controlled to make the enclosure temperature match the weighted sum $(KT_{ss}+(1-K)T_{rr})$ of the sample and reference pan temperatures. As shown in FIG. 2, the measurement and enclosure heating assemblies are coupled to a cooling device.

In the embodiment shown in FIG. 5, DSC module 200 includes $T_0$, $\Delta T$, $\Delta T0$ and $T_e-T_s$ amplifiers 201a, 201b, 201c and 201d respectively that receive inputs from $T_0$, $T_s$, $T_r$ and $T_e$ thermocouples as shown and described in FIG. 3. The output from the $T_0$, $\Delta T$, $\Delta T_0$ and $T_e-T_s$ amplifiers are converted from analog to digital signals by A/D convertors 202a, 202b, 202c and 202d. The output of the A/D convertors is supplied to embedded microprocessor 230. Embedded microprocessor comprises thermocouple lookup application 231, sensor coefficient application 232, contact resistance model 233, heat flow calculation 234, temperature control algorithm 235 and data storage function 236.

Thermocouple Lookup 231 is a program resident in embedded microprocessor 230 that converts the digital signal representing the output signal of the $T_0$ thermocouple to a temperature. The temperature at the terminals of the $T_0$ thermocouple is measured by a thermistor and that temperature is converted to the equivalent voltage of the thermocouple at that temperature. The equivalent thermocouple voltage is summed with the output of the $T_0$ thermocouple. The resultant reference junction compensated voltage is converted to temperature by using a thermocouple lookup table that is based on NIST monograph 175. Digital signals representing temperature difference measurements $\Delta T$, $\Delta T_0$ and $T_e-T_s$ are converted to temperature units by applying the Seebeck coefficients to the signals representing the voltage at the terminals of the respective temperature differences. Reference junction compensation is not needed when measuring temperature differences. In this embodiment, the Seebeck coefficients are based on NIST monograph 175.

Sensor Coefficients 232 is a program resident in embedded microprocessor 230 that supplies sensor coefficients $R_s$, $R_r$, $C_s$, $C_r$ used in the heat flow calculation. The temperature of the DSC cell as indicated by the $T_0$ thermocouple is used to determine the appropriate value for each of the coefficients. Sensor coefficients are determined using the calibration procedures disclosed herein and saved in the module in tabular form. The program supplies the sensor coefficients to heat flow calculation program 234.

Contact Resistance Model 233 is a program resident in embedded microprocessor 230 that calculates the pan contact resistance using the thermal contact resistance model equation disclosed in the '747 patent.

Heat flow calculator 234 is a program resident in embedded microprocessor 230 that calculates heat flow rates using the methods disclosed herein. Sensor coefficients required by the program are supplied by sensor coefficient program 232 and contact resistances needed by the program are supplied by contact thermal resistance model program 233.

Temperature control 235 is a program resident in embedded microprocessor 230 that determines the power to be supplied to the measurement assembly heater and the power to be supplied to the enclosure assembly heater as shown in FIG. 4. In one embodiment of the present invention, Temperature Control program 235 operates according to a PID (proportional-integral-derivative) control scheme. Power is supplied to the measurement assembly heater to cause the measurement assembly to follow the desired experimental temperature program. Power is supplied to the enclosure heater assembly to cause the enclosure temperature to match a weighted average of sample and reference container temperatures as disclosed herein.

Data storage 236 is nonvolatile storage within the module that stores the data file of the experiment.

In an embodiment, embedded microprocessor 230 is in communication over, e.g., an Ethernet network 30, with computer 300 which comprises instrument control interface module 302, data analysis module 303 and data storage module 304.

Instrument Control Interface 302 is a program resident in computer 300 that provides the user interface to module 200. It is used to program the thermal method for the experiment, to select any options and to control the instrument, e.g., start and stop experiments, select purge gas flow rates, select instrument mode (for example MDSC or standard DSC), and supply information to autosamplers if applicable.

Data Analysis 303 is a program resident in computer 300 that is used to display and process the results of the experiment. The user may select the signals to be displayed and display options such as axis scaling and selection of the abscissa. Analysis of the results may also be performed, such as integration of the area of a peak to determine the enthalpy of a transition.

Data Storage 304 is nonvolatile storage of the data file and the experimental results, e.g., a hard-disk drive or a non-volatile solid-state memory.

While various embodiments have been described above, the description is intended to be exemplary, rather than limiting. It will be apparent to those of ordinary skill in the art that additional embodiments and implementations are possible. Accordingly, the embodiments are not to be restricted except in light of the attached claims and their equivalents.

What is claimed is:

1. A method of measuring a differential heat flow in a differential scanning calorimeter, wherein the differential scanning calorimeter comprises a block of high thermal conductivity material within an enclosure, said block of high thermal conductivity material comprising a sample measuring system and a reference measuring system, said method comprising:

measuring a temperature of the enclosure;
controlling the temperature of the block of high thermal conductivity material according to a predetermined temperature program;
measuring $T_0$, $\Delta T$, $\Delta T_0$, and $T_e$, where $T_0$ is the temperature of the block of high thermal conductivity material, $\Delta T$ is the difference between the temperature of the sample measuring system and the temperature of the reference measuring system, $\Delta T_0$ is the difference between the temperature of the block of high thermal conductivity material and the temperature of the sample measuring system, and $T_e$ is the temperature of the enclosure;
calculating a temperature of a sample container in the sample measuring system and a temperature of a reference container in the reference measuring system based upon the measured values of $T_0$, $\Delta T$ and $\Delta T_0$;
controlling the temperature of the enclosure to follow a weighted average of the calculated temperature of the sample container and the calculated temperature of the reference container to minimize heat leakage between the sample and reference measuring systems and the enclosure; and
calculating a differential heat flow to the sample container with respect to a heat flow to the reference container based upon measuring $\Delta T$, $\Delta T_0$, $T_a$ and $T_e$ by using an algorithm that comprises corrections to the measured heat flow to the sample container based in part upon the difference between the temperature of the enclosure and the temperature of the sample container.

2. The method of claim 1, wherein the step of calculating a differential heat flow to the sample container with respect to the reference container comprises using one of the following equation and any other algebraically equivalent equations to the following equation:

$$q = q_s\left(1 + \frac{R_{ss}}{R_{se}}\right) + \frac{T_e - T_s}{R_{se}} - \frac{m_{ps}}{m_{pr}} \frac{\dot{T}_{ss}}{\dot{T}_{rr}}\left(q_r\left(1 + \frac{R_{rr}}{R_{re}}\right) + \frac{T_e - T_s + \Delta T}{R_{re}}\right)$$

where:
q is the differential heat flow rate to the sample container with respect to the heat flow to the reference container;
$q_s$ is the measured sample heat flow rate;
$q_r$ is the measured reference heat flow rate;
$R_{ss}$ is the thermal contact resistance between the sample container and its calorimeter;
$R_{rr}$ is the thermal contact resistance between the reference container and its calorimeter;
$R_{se}$ is the thermal resistance between the sample container and the enclosure;
$R_{re}$ is the thermal resistance between the reference container and the enclosure;
$T_e$ is the temperature of the enclosure;
$T_s$ is the temperature of the sample measuring system;
$m_{ps}$ is the mass of the sample container;
$m_{pr}$ is the mass of the reference container;
$\dot{T}_{ss}$ is the sample container heating rate;
$\dot{T}_{rr}$ is the reference container heating rate; and
$\Delta T$ is equal to $T_s - T_r$, where $T_r$ is the temperature of the reference measuring system.

3. The method of claim 1, further comprising calibrating the differential scanning calorimeter by conducting a first constant heating rate experiment with empty containers and a second constant heating rate experiment at the same constant heating rate as in the first experiment with a sample of known heat capacity in the sample container and a similar sample of known thermal conductivity in the reference container.

4. The method of claim 1, wherein the differential scanning calorimeter comprises a base structure comprising a first flange and a second flange, further comprising thermal resistors in the form of slender cylindrical rods joining the first flange to the second flange.

5. The method of claim 1, wherein the weighted average uses a weighting factor which is greater than or equal to zero and less than or equal to 1.

6. The method of claim 1, wherein the weighted average of the calculated temperature of the sample container and the calculated temperature of the reference container is a straight average.

7. A method of measuring heat flow in a differential scanning calorimeter having a measuring system comprising a sample container and a reference container, and an enclosure comprising:
controlling a temperature of the measuring system;
controlling a temperature of the enclosure independently of the temperature of the measuring system using a set point temperature which is an average of the sample container temperature and the reference container temperature to minimize heat leakage between the sample and reference containers and the enclosure; and
performing the step of determining the differential heat flow to a sample container of the differential scanning calorimeter compared to a reference container of the differential scanning calorimeter,
wherein the differential scanning calorimeter comprises a first thermocouple attached to the enclosure of the measuring system, a second thermocouple attached to a base structure of the differential scanning calorimeter, a third thermocouple attached to a sample position of the measuring system and a fourth thermocouple attached to a reference position of the measuring system.

8. The method of claim 7, wherein the measuring system comprises a sample measuring system and a reference measuring system.

9. The method of claim 7, further comprising the step of determining a sample calorimeter thermal resistance, a sample calorimeter heat capacity, a reference calorimeter thermal resistance, and a reference calorimeter heat capacity.

10. The method of claim 7, wherein the base structure comprises a first flange and a second flange, and thermal resistors in the form of slender cylindrical rods joining the first flange to the second flange.

11. The method of claim 10, wherein the first flange is in thermal contact with a heating element and the second flange is in thermal contact with a cooling device.

12. A differential scanning calorimeter comprising:
a block of high thermal conductivity material comprising a sample measuring system and a reference measuring system;
an enclosure encompassing the block of high thermal conductivity material, the sample measuring system and the reference measuring system;
a first thermocouple attached to the enclosure for measuring a temperature of the enclosure $T_e$;
a second thermocouple attached to the block of high thermal conductivity material for measuring a temperature of the block of high thermal conductivity material $T_0$;
a third thermocouple attached to the sample measuring system;
a fourth thermocouple attached to the reference measuring system,
wherein said second, third and fourth thermocouples are configured to measure $\Delta T_0$ and $\Delta T$, where $\Delta T$ is the difference between the temperature of the sample measuring system and the temperature of the reference measuring system, and where $\Delta T_0$ is the difference between the temperature of the sample measuring system and the temperature of the block of high thermal conductivity material;
a computer system comprising a module for controlling the temperature of the enclosure, a module for controlling the temperature of the block of high thermal conductivity material, a module for calculating a thermal resistance of the sample measuring system, a heat capacity of the sample measuring system, a thermal resistance of the reference measuring system, a heat capacity of the reference measuring system;
the computer system receiving inputs from the first, second, third and fourth thermocouples representative of $T_0$, $\Delta T$, $\Delta T_0$, and $T_e$, where $T_0$ is the temperature of the block of high thermal conductivity material, $\Delta T$ is the difference between the temperature of the sample measuring system and the temperature of the reference measuring system, $\Delta T_0$ is the difference between the temperature of the block of high thermal conductivity material and the temperature of the sample measuring system, and $T_e$ is the temperature of the enclosure;
wherein the computer system is programmed to calculate a temperature of a sample container in the sample measuring system and a temperature of a reference container in the reference measuring system based upon the measured values of $T_0$, $\Delta T$ and $\Delta T_0$;
wherein the computer system is programmed to control the temperature of the enclosure to follow a weighted average of the calculated temperature of the sample container and the calculated temperature of the reference container to minimize heat leakage between the sample and reference measuring systems and the enclosure; and
wherein the computer system is programmed to calculate a differential heat flow to the sample container with respect to a heat flow to the reference container based upon measuring $\Delta T$, $\Delta T_0$, $T_s$, and $T_e$ by using an algorithm that comprises corrections to the measured heat flow to the sample container based in part upon the difference between the temperature of the enclosure and the temperature of the sample container.

13. The differential scanning calorimeter of claim 12, wherein the computer system calculates a differential heat flow to the sample container with respect to the reference container comprises using one of the following equation and any other algebraically equivalent equations to the following equation:

$$q = q_s\left(1 + \frac{R_{ss}}{R_{se}}\right) + \frac{T_e - T_s}{R_{se}} - \frac{m_{ps}}{m_{pr}}\frac{\dot{T}_{ss}}{\dot{T}_{rr}}\left(q_r\left(1 + \frac{R_{rr}}{R_{re}}\right) + \frac{T_e - T_s + \Delta T}{R_{re}}\right)$$

where:
q is the differential heat flow rate to the sample container with respect to the heat flow to the reference container;
$q_s$ is the measured sample heat flow rate;
$q_r$ is the measured reference heat flow rate;
$R_{ss}$ is the thermal contact resistance between the sample container and its calorimeter;
$R_{rr}$ is the thermal contact resistance between the reference container and its calorimeter;

$R_{se}$ is the thermal resistance between the sample container and the enclosure;
$R_{re}$ is the thermal resistance between the reference container and the enclosure;
$T_e$ is the temperature of the enclosure;
$T_s$ is the temperature of the sample measuring system;
$m_{ps}$ is the mass of the sample container;
$m_{pr}$ is the mass of the reference container;
$\dot{T}_{ss}$ is the sample container heating rate;
$\dot{T}_{rr}$ is the reference container heating rate; and
$\Delta T$ is equal to $T_s - T_r$, where $T_r$ is the temperature of the reference measuring system.

14. The differential scanning calorimeter of claim 12, wherein the differential scanning calorimeter comprises a base structure comprising a first flange and a second flange, further comprising thermal resistors in the form of slender cylindrical rods joining the first flange to the second flange.

15. The differential scanning calorimeter of claim 12, wherein the enclosure is a closed-end hollow cylinder with an integral flange that is in thermal contact with a heating/cooling assembly.

16. The differential scanning calorimeter of claim 12, wherein the block of high thermal conductivity material is a block of one of silver, gold, aluminum and copper.

17. A quasiadiabatic differential scanning calorimeter having an enclosure and a DSC sensor comprising:
    means for independently measuring the temperature of the enclosure and the temperature of the DSC sensor;
    means for controlling a temperature of the enclosure to supress heat flow leakage between the DSC sensor and the enclosure leaving only a residual heat flow leakage; and
    a heat flow measurement algorithm that accounts for the residual heat flow leakage between the DSC sensor and the enclosure to determine the heat flow balance within the calorimeter,
    wherein said algorithm includes terms representative of the temperature of the enclosure and the temperature of the DSC sensor.

\* \* \* \* \*

UNITED STATES PATENT AND TRADEMARK OFFICE
CERTIFICATE OF CORRECTION

Page 1 of 1

PATENT NO. : 9,857,241 B2
APPLICATION NO. : 14/425473
DATED : January 2, 2018
INVENTOR(S) : Robert L. Danley It is certified that error appears in the above-identified patent and that said Letters Patent is hereby corrected as shown below:

In the Drawings

FIG. 3:
Replace "ASSMEBLY" with "ASSEMBLY".

In the Specification

Column 6, Line 64:
Replace "$q_m = b(C_{ss} + C_{am} - C_{rr})$" with "$q_m = b(C_{ss} + C_{sm} - C_{rr})$".

Column 7, Line 38:
Replace "$T_0 - T_s$" with "$T_0 - T_e$".

Column 12, Line 52:
Replace "$\Delta T, \Delta T$" with "$\Delta T, \Delta T_0$".

Column 14, Line 30:
Replace "$T_0, \Delta T, \Delta T0$" with "$T_0, \Delta T, \Delta T_0$".

Signed and Sealed this
Twenty-third Day of July, 2019

Andrei Iancu
*Director of the United States Patent and Trademark Office*